US012779151B2

(12) United States Patent
Petit

(10) Patent No.: US 12,779,151 B2
(45) Date of Patent: Nov. 3, 2026

(54) DEVICE FOR NASAL DELIVERY OF POWDER

(71) Applicant: APTAR FRANCE SAS, Le Neubourg (FR)

(72) Inventor: Ludovic Petit, Vitot (FR)

(73) Assignee: APTAR FRANCE SAS, Le Neubourg (FR)

( * ) Notice: Subject to any disclaimer, the term of this patent is extended or adjusted under 35 U.S.C. 154(b) by 599 days.

(21) Appl. No.: 18/284,778

(22) PCT Filed: Mar. 28, 2022

(86) PCT No.: PCT/FR2022/050576
§ 371 (c)(1),
(2) Date: Sep. 28, 2023

(87) PCT Pub. No.: WO2022/208014
PCT Pub. Date: Oct. 6, 2022

(65) Prior Publication Data

US 2024/0157069 A1 May 16, 2024

(30) Foreign Application Priority Data

Mar. 29, 2021 (FR) ....................................... 2103161

(51) Int. Cl.
*A61M 15/08* (2006.01)

(52) U.S. Cl.
CPC ....... *A61M 15/08* (2013.01); *A61M 2202/064* (2013.01); *A61M 2205/073* (2013.01)

(58) Field of Classification Search
CPC .... A61M 15/08; A61M 11/007; A61M 11/02; A61M 2205/073
See application file for complete search history.

(56) References Cited

U.S. PATENT DOCUMENTS

| | | | |
|---|---|---|---|
| 4,017,007 A | 4/1977 | Riccio | |
| 5,395,032 A | 3/1995 | Fuchs | |
| 2019/0358417 A1 * | 11/2019 | Brouet | .................. A61M 11/02 |

FOREIGN PATENT DOCUMENTS

| | | |
|---|---|---|
| EP | 0407276 A2 | 1/1991 |
| EP | 0575239 A1 | 12/1993 |

(Continued)

OTHER PUBLICATIONS

International Preliminary Report on Patentability (with translation of the Written Opinion) issued Oct. 3, 2023 in Application No. PCT/FR2022/050576.

(Continued)

*Primary Examiner* — Margaret M Luarca
(74) *Attorney, Agent, or Firm* — Sughrue Mion, PLLC

(57) ABSTRACT

Device having a reservoir containing a dose of powder, a head having an orifice, an actuating member displaceable with respect to the head, and an air vent generating a flow of compressed air for delivering the dose of powder into the nostril through the orifice. The air vent has a chamber, formed by a cylinder, and a piston which slides sealingly within the cylinder in order to compress the air contained in the chamber. The device has an insert forming the piston and interacting sealingly, in a rest position, with the reservoir, the insert being axially displaceable with respect to the reservoir between its rest position and an actuation position, in which it no longer interacts sealingly with the reservoir.

5 Claims, 1 Drawing Sheet

(56) References Cited

FOREIGN PATENT DOCUMENTS

Figure 1:
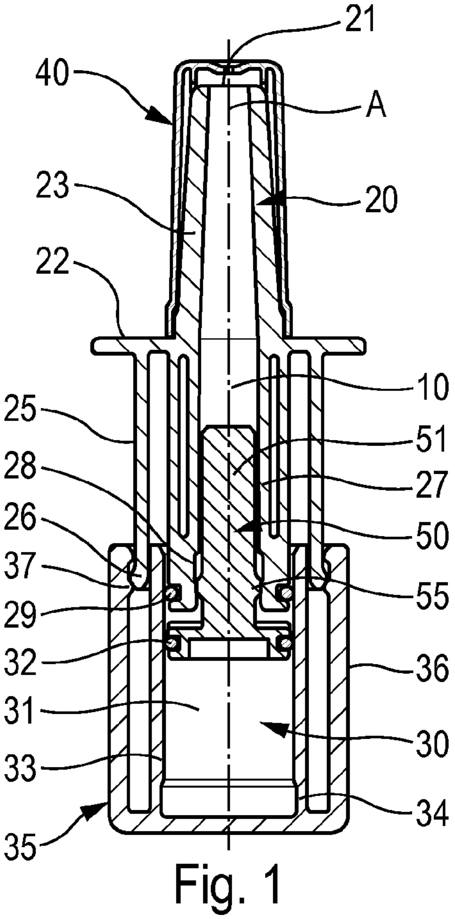

| | | | |
|---|---|---|---|
| EP | 3682922 | A1 | 7/2020 |
| WO | 93/11818 | A1 | 6/1993 |
| WO | 99/46055 | A1 | 9/1999 |
| WO | 02/45866 | A1 | 6/2002 |
| WO | 2005/120617 | A1 | 12/2005 |
| WO | 2007/141203 | A1 | 12/2007 |
| WO | 2015/001281 | A1 | 1/2015 |
| WO | 2017/118827 | A1 | 7/2017 |
| WO | 2019/220062 | A1 | 11/2019 |

OTHER PUBLICATIONS

International Search Report of PCT/FR2022/050576 dated May 31, 2022 [PCT/ISA/210].

* cited by examiner

DEVICE FOR NASAL DELIVERY OF POWDER

CROSS REFERENCE TO RELATED APPLICATIONS

This application is a National Stage of International Application No. PCT/FR2022/050576 filed on Mar. 28, 2022, claiming priority based on French Patent Application No. 2103161 filed on Mar. 29, 2021.

The present invention relates to a device for nasal delivery of powder.

The devices for nasal delivery of powder are well-known. They generally have a reservoir containing one or more doses of powder, delivery means, and a nasal delivery head intended to be inserted into a nostril of a user, said nasal delivery head having a delivery orifice. The delivery means generally have an air expeller. When the delivery device is actuated, a dose of powder is delivered into a nostril of a user by means of a flow of air generated by the air expeller.

A disadvantage with these devices of the prior art relates to the complexity of the device, in particular, the number of parts to be manufactured and assembled.

Another disadvantage relates to the reliability of the device, which can highly depend on the way in which the user actuates the device. Thus, the performance of the air expeller can be dependent on the user, for example on the force and/or on the actuation speed, which is not always optimal.

Documents U55395032, U54017007, EP3682922, EP0407276, EP0575239, WO9311818, WO9946055, WO0245866, WO2005120617, WO2007141203, WO2015001281, WO2017118827 and WO2019220062 describe devices of the prior art.

The present invention aims to provide a device for nasal delivery of powder which does not reproduce the above-mentioned shortcomings.

The present invention aims to provide a device for nasal delivery of powder which is reliable to use.

The present invention also aims to provide a device for nasal delivery of powder wherein the performance of the air expeller is substantially independent of the user and of its way in actuating the device.

The present invention also aims to provide a device for nasal delivery of powder which is simple and inexpensive to manufacture and to assemble.

The present invention therefore relates a device for nasal delivery of powder having a reservoir containing one single dose of powder, a nasal delivery head having a delivery orifice intended to be inserted into a nostril of a user, an actuating member axially displaceable with respect to said head during the actuation of said device, and an air expeller generating, during actuation, a flow of compressed air for delivering said dose of powder into said nostril through said delivery orifice, said air expeller comprising an air chamber, formed by a hollow axial cylinder, and an air piston which, during actuation, slides sealingly into said hollow axial cylinder to compress the air contained in said air chamber, said device having an endpiece forming said air piston and interacting sealingly in a rest position with said reservoir, said endpiece being axially displaceable with respect to said reservoir between its rest position and an actuation position, in which it no longer interacts sealingly with said reservoir, said reservoir having a cylindrical part of said delivery head, said cylindrical part having in its lower part, a radial recess on its radially internal surface and a piston on its radially external surface, said endpiece having a central body provided with a radial shoulder projecting radially outwards, said radial shoulder interacting sealingly in a rest position with a lower axial end of said cylindrical part of said delivery head and interacting with said radial recess in an actuation position.

Advantageously, said device has a removable cap which, in a rest position, closes and protects said delivery orifice and therefore the dose of powder contained in said reservoir.

Advantageously, said hollow axial cylinder of said air expeller is integral with said actuating member slidingly mounted with respect to said delivery head.

Advantageously, said hollow cylinder of said air expeller has, at a lower axial end, a radial cutout forming a cylinder part of a greater diameter, such that said air piston interacts sealingly with said hollow cylinder, until it reaches said cutout, where it no longer interacts sealingly, enabling the compressed air to be discharged from said air chamber to form said flow of compressed air used to expel said dose of powder from said reservoir.

Advantageously, said insert is displaced from its rest position to its actuation position at the start of the actuation stroke, and said flow of compressed air is generated at the end of the actuation stroke.

Figure 2:
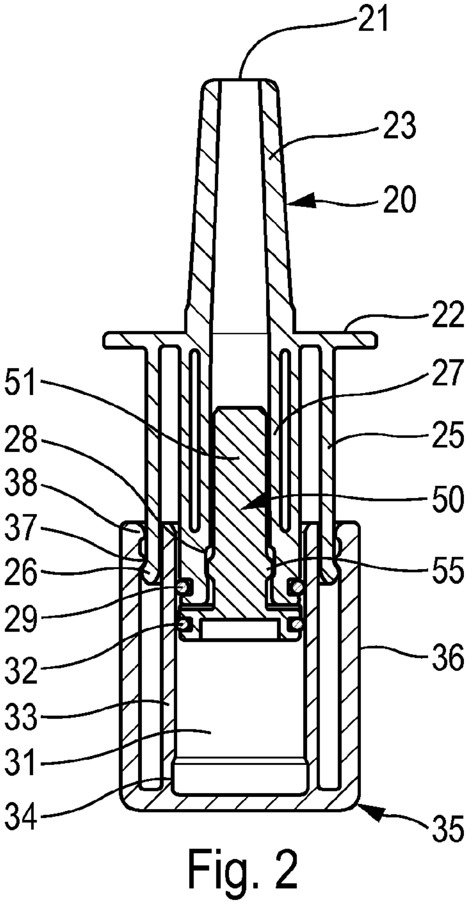
Figure 3:
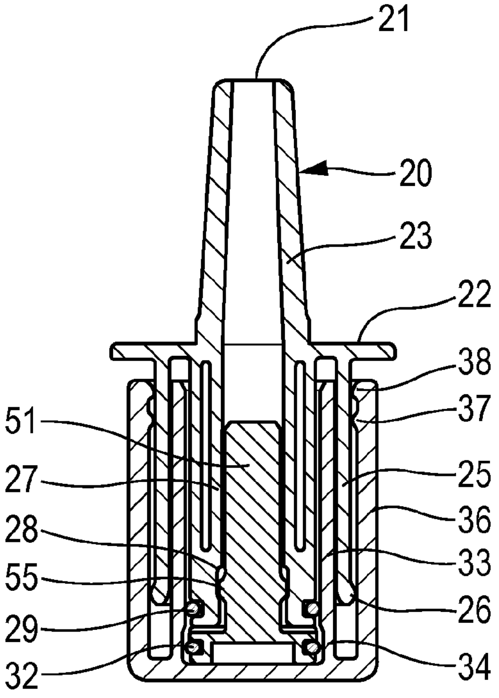

These features and advantages and others will appear more clearly during the detailed description below, made in reference to the accompanying drawings, given as non-limiting examples, and in which:

FIG. 1 is a schematic cross-sectional view of a device for nasal delivery of powder according to an advantageous embodiment, in a rest position before actuation, FIG. 2 is a view similar to that of FIG. 1, at the start of actuation, and FIG. 3 is a view similar to those of FIGS. 1 and 2, at the end of actuation.

In the description, the terms "axial" and "radial" refer to the longitudinal axis A of the device shown in FIG. 1. The terms "top", "bottom", "upper" and "lower" refer to the upright position of the device shown in the drawings.

The invention applies to devices of the unidose powder type such as that represented in the figures. Naturally, other types of unidose devices can also be considered.

The device shown in the figures has a reservoir 10 containing one single dose of powder.

A nasal delivery head 20 is associated with the reservoir 10, said head being intended to be inserted into a nostril of a user. The nasal delivery head 20 has a delivery orifice 21, preferably axially oriented. It also advantageously has a finger rest 22 extending radially to facilitate the actuation. A nasal endpiece 23 extends axially upwards from said finger rest 22 and ends at said delivery orifice 21. This nasal endpiece 23 is of reduced radial dimension to be able to be inserted into a nostril at the time of actuation. On the opposite side of the finger rest 22, a skirt 25 extends axially downwards from said finger rest 22.

The reservoir 10 is defined at least partially by a cylindrical part 27 of the delivery head 20. As can be seen in the drawings, this cylindrical part 27 is advantageously radially disposed inside the skirt 25 by being coaxial to it. In its lower part, the cylindrical part 27 has on its radially internal surface, a radial recess 28 and on its radially external surface, a piston 29, the functions of which will be described below. In the example of the figures, the piston 29 has an O-ring fixed in a suitable housing, but it could be made in any suitable way, for example in the well-known form of a sealing lip.

The device further has an air expeller 30 generating, during actuation, a flow of compressed air to deliver the dose of powder into said nostril through the delivery orifice 21. The air expeller 30 comprises an air chamber 31 and an air piston 32 sliding sealingly into said air chamber 31 to compress the air contained in said air chamber 31 and thus generate said flow of compressed air.

The air chamber 31 is formed by a hollow axial cylinder 33 which is integral, preferably as one-piece, with an actuating member 35 slidingly mounted with respect to the delivery head 20. The lower axial side of said hollow cylinder 33 is closed and its upper side is open and blocked by said air piston 32.

The hollow cylinder 33 has, at its lower axial end, a radial cutout 34 which forms a cylinder part of a greater diameter. Thus, the air piston 32 interacts sealingly with the hollow cylinder 33 until it reaches said cutout 34, where it no longer interacts sealingly, enabling the compressed air from being discharged to form the flow of compressed air of the air expeller used to expel the dose of powder from the reservoir.

The actuating member 35 has an external sleeve 36 coaxial to said hollow cylinder 33 and defining a space between them.

The skirt 25 is advantageously slidingly disposed in the space defined between said hollow cylinder 33 and said external sleeve 36. In this implementation, the external sleeve 36 and/or the hollow cylinder 33 can have precompression means 37, such as one or more radial projection(s), interacting with said skirt 25. These precompression means 37 require, to be overcome, that the user exerts a predetermined actuation force.

Advantageously, the skirt 25 has, at its lower axial end, a radial profile 26 interacting with said precompression means 37 at very beginning of actuation. Typically, from a predetermined actuation force, the radial profile 26 of the skirt 25 can pass above the radial projection 37. Such a precompression in the hand of the user released suddenly, ensures that the actuation will be done completely, without risk of a partial actuation.

Advantageously, the external sleeve 36 and/or the hollow cylinder 33 can have retaining means 38, such as one or more radial projection(s), to ensure the holding of the delivery head 20 on the actuation member 35.

In a rest position, the radial profile 26 of the skirt 25 is advantageously wedged between the projections 37 and 38 of the actuating member 35.

In the example shown in the figures, the reservoir 10 is formed inside the delivery head 20, and is open at its two axial ends. In a rest position, the reservoir 10 is closed at its upper axial end by a removable cap 40, which can be seen in FIG. 1. This cap 40 serves to close and protect the delivery orifice 21 and the reservoir 10, and therefore the dose of powder that it contains. The lower axial end of the reservoir 10 is closed by an insert 50.

This insert 50 has a central body 51 provided with a radial shoulder 55 projecting radially outwards. The radial shoulder 55 interacts sealingly in a rest position, with the lower axial end of the cylindrical part 27 of the delivery head 20. During actuation, the endpiece 50 is slightly axially displaced upwards with respect to the head 20 to its actuation position, in which the radial shoulder 55 thus interacts with the radial recess 28. In this actuation position, the flow of air generated by the air expeller 30 can thus pass around said radial shoulder 55 and drive with it, the powder contained in the reservoir 10.

The air piston 32 of the air expeller 30 is advantageously formed on said endpiece 50.

In the example of the figures, the air piston 32 has an O-ring fixed in a suitable housing of said endpiece 50, but it could be made in any suitable way, for example in the well-known form of a sealing lip.

The operation of the delivery device will now be described in reference to the figures.

In a rest position, which can be seen in FIG. 1, the dose of powder disposed in the reservoir 10 is protected, on the one hand, by the removable cap 40 positioned on the head 20, and on the other hand, by the insert 50 in a sealed blocking position, with respect to the head 20.

When a user wishes to use the device, they remove the removable cap 40 and insert the nasal endpiece 23 of the head 20 into a nostril.

To actuate the device, they place their fingers on the finger rest 22 of the head 20 and the thumb on the bottom of the actuating member 35, and exert an axial actuation force between their fingers and their thumb. The precompression means 37 obligate the user to exert a predetermined force to trigger the actuation.

When this predetermined force is exerted, the head 20 can be axially displaced downwards with respect to the actuating member 35. The resistance exerted by the air chamber 31 on the air piston 32 being greater than that exerted by the head 20 on the insert 50, at the start of actuation, the endpiece 50 does not move with respect to the actuating member 35, and it is the head which is slightly displaced with respect to the actuating member 35 and with respect to the insert 50. This has the effect of displacing the insert 50 from its sealed blocking position into its actuation position in which the radial shoulder 55 is disposed in the radial recess 28, as can be seen in FIG. 2.

In this position, the lower axial end of the cylindrical part 27 of the head 20 come into contact with the air piston 32, and a continuation of the axial displacement of the head 20 with respect to the actuating member 35 will therefore axially displace the insert 50 with respect to the actuating member 35, with consequently a displacement of the air piston 32 in the air chamber 31, which compresses the air contained in the air chamber.

When the air piston 32 reaches the radial cutout 34, at the end of the actuation stroke, the compressed air can be discharged from the air chamber 31 to expel the dose of powder contained in the reservoir 10.

The present invention therefore makes it possible to produce a unidose powder delivery device with only three constitutive parts, namely the delivery head 20, the actuating member 35 and the insert 50, and a removable part, namely the cap 40. The manufacturing and the assembly of the device are therefore particularly simple and inexpensive.

In addition, the air expeller is independent from the user, as whatever the actuation force or speed, the flow of compressed air is only released at the end of the actuation stroke, therefore always with the same performance, in particular in terms of pressure and flow rate.

The present invention has been described in reference to an advantageous embodiment, but it is understood that a person skilled in the art can apply any modifications to it, without going beyond the scope of the present invention such as defined by the accompanying claims.

The invention claimed is:

1. A device for nasal delivery of powder having a reservoir containing one single dose of powder, a nasal delivery head having a delivery orifice intended to be inserted into a nostril of a user, an actuating member axially displaceable with respect to said head during the actuation of said device, and an air expeller generating, during the actuation, a flow of compressed air to deliver said dose of powder into said nostril through said delivery orifice, said air expeller comprising an air chamber, formed by a hollow axial cylinder, and an air piston, which during actuation, slides sealingly into said hollow axial cylinder to compress the air contained in said air chamber, said device having an insert forming said air piston and interacting sealingly in a rest position with said reservoir, said insert being axially displaceable with respect to said reservoir between said rest position and an actuation position, in which said insert no longer interacts sealingly with said reservoir, characterised in that said reservoir has a cylindrical part of said delivery head, said cylindrical part having in a lower part, a radial recess on its a radially internal surface and a piston on a radially external surface, said insert having a central body provided with a radial shoulder projecting radially outwards, said radial shoulder interacting sealingly in a rest position with a lower axial end of said cylindrical part of said delivery head and interacting in an actuation position with said radial recess.

2. The device according to claim 1, comprising a removable cap which, in a rest position, closes and protects said delivery orifice and therefore the dose of powder contained in said reservoir.

3. The device according to claim 1, wherein said hollow axial cylinder of said air expeller is integral with said actuating member slidingly mounted with respect to said delivery head.

4. The Device according to claim 1, wherein said hollow cylinder of said air expeller has, at a lower axial end, a radial cutout forming a cylinder part of a greater diameter, such that said air piston interacts sealingly with said hollow cylinder until said air piston reaches said cutout, where said air piston no longer interacts sealingly, enabling the compressed air to be discharged from said air chamber to form said flow of compressed air used to expel said dose of powder from said reservoir.

5. The device according to claim 1, wherein said insert is displaced from a rest position to an actuation position at the start of the displacement of said actuating member, and said flow of compressed air is generated at the end of the displacement of said actuating member.

* * * * *